United States Patent [19]

Powell

[11] Patent Number: 4,536,413

[45] Date of Patent: Aug. 20, 1985

[54] LEATHER COVERING GRIP ENHANCEMENT

[76] Inventor: Philip R. Powell, 408 S. 7th, Ponca City, Okla. 74601

[21] Appl. No.: 609,639

[22] Filed: May 14, 1984

[51] Int. Cl.³ .............................................. B05D 1/00
[52] U.S. Cl. ...................................... 427/11; 424/68; 427/389; 427/444
[58] Field of Search ................ 427/11, 444, 323, 389, 427/384; 252/8.57; 424/68

[56] References Cited

U.S. PATENT DOCUMENTS 4,062,938 12/1977 Gary et al. ............................ 424/68
4,125,600 11/1978 Callingham ........................... 424/68
4,127,694 11/1978 Murphy et al. ....................... 427/11
4,209,549 6/1980 Murphy et al. ....................... 427/11

*Primary Examiner*—Sadie L. Childs
*Attorney, Agent, or Firm*—Dunlap & Codding

[57] ABSTRACT

A composition and method of using thereof for enhancing the tactile characteristics of leather covered handles. The composition comprises an antiperspirant, a nonionic polymeric ethoxylate surfactant and solvent, and is applied to the leather which is subsequently dried with a cloth. The composition may also be applied to the hands of one about to use the handles, and the solvent permitted to evaporate therefrom.

12 Claims, No Drawings

LEATHER COVERING GRIP ENHANCEMENT

BACKGROUND OF THE INVENTION

In the performance of many sports, including tennis, racquet ball, badminton and golf, for example, racquets or clubs must be securely and comfortably grasped and manipulated. In cases with the more rigorously athletic sports, the manipulative grasping of a single racquet may continue almost uninterruptedly for hours.

The handles of high quality racquets and clubs are usually covered with leather, processed cowhide leather being most preferably used. Such processed leather is prepared to maximize tactile properties such as suppleness and frictional texture.

When leather covered handles of sports implements such as, for example, racquet ball racquets and tennis racquets, are subjected to rigorous usage, the handles often become coated with oils and perspiration from the hands of those playing these sports. This oil and perspiration coating decreases the suppleness and frictional texture of the leather handles, sometimes to the extent of negatively affecting sureness of the player's grip. Although leather predominates as the preferred covering for sports implement handles, other at least partially porous coverings such as certain cloths or plastics may sometimes be utilized and sometimes display similar problems due to oil and perspiration.

There are four general categories of previously available grip-enhancement products. These categories are: powders and sprays; disposable overwraps; synthetic replacement grips; and slip-on grips. While each of these grip-enhancement products may produce useful results, particularly in unique playing conditions, it is generally acknowledged that none of them give a result favorably comparable with a fresh, top-quality leather grip. When some commercially available powders and sprays have been used with tennis racquets, there has been reported a tendency to produce one of the following results: no enhancement of leather tactile characteristics; temporary and less than optimal enhancement of leather tactile characteristics; or an overenhancement of the leather covered handle tactile characteristics, namely a stickiness which inhibited shifts from forehand to backhand grips.

The composition of the present invention and method of use thereof provide a manner of virtually rejuvenating the tactile characteristics of a leather covering, without adding unwanted bulkiness or stickiness to said leather covering. Further, the use of the present invention also inhibits hand perspiration during rigorous play, also enhancing sureness of grip. These qualities resulting from the use of the present invention are notably superior to gripping qualities obtainable with previously utilized powders, sprays or other leather covering emollients. The present invention may also be applicable in enhancing the tactile characteristics of other types of handle coverings, if such handle coverings are at least partially porous and have their tactile characteristics diminished by oils or perspiration.

One special component of the present invention is a nonionic polymeric ethoxylate surfactant ("degreasing" agent), which appears to substantially remove oils from a leather covering. Another important component of the present invention is an anti-perspirant, to inhibit hand perspiration from forming during play.

SUMMARY OF THE INVENTION

A composition for enhancing the tactile characteristics of a leather covering. The composition comprises between about 10 volume percent and about 99.9 volume percent non-ionic polymeric ethoxylate surfactant; at least about 0.1 weight percent antiperspirant inorganic compound; and up to about 89.9 volume percent dermatologically acceptable volatile solvent.

DETAILED DESCRIPTION OF THE PREFERRED EMBODIMENT

The combination of an antiperspirant inorganic compound, a nonionic polymeric ethoxylate surfactant ("degreasing" agent) and a dermatologically acceptable volatile solvent was discovered to produce a composition of unprecedented effectiveness in enhancing the "gripability" or tactile characteristics of sports racquets or clubs, even during episodes of rigorous sports activity during very hot weather.

The antiperspirant inorganic compound preferably used in the practice of the present invention is aluminum chloride hexahydrate ($AlCl_3.6H_2O$) although there are many other forms of antiperspirant inorganic compounds which should also be effective, alone or in combinations, for example, aluminum chlorohydrate ($[Al_2(OH)_5Cl]_x$), aluminum hydroxychloride ($Al_2(OH)_3Cl.2H_2O$ or $[Al(OH)_2Cl]_x$), aluminum sulfate octahydrate ($Al_2O_{12}S_3.8H_2O$), aluminum potassium sulfate ($Al_2(SO_4)_3.K_2SO_4.24H_2O$), basic aluminum bromide ($Al_2(OH)_5Br.3H_2O$) and combinations of hydrous zirconyl chloride ($ZrOOHCl.xH_2O$) and hydrated aluminum chloride. The concentrations of antiperspirant in the composition of the present invention may vary widely, from a minimum of about 0.1 weight percent to up to about 15 weight percent, although a preferred concentration is 0.5 weight percent.

A nonionic polymeric ethoxylate surfactant found to be particularly preferable for practice of the present invention is a nonionic polymeric ethoxylate with an alkyl pendant group and having the formula:

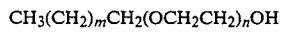

$$CH_3(CH_2)_mCH_2(OCH_2CH_2)_nOH$$

where m is between about 4 and about 16 and n is between about 3 and about 11. Such non-ionic polymeric ethoxylates are available, for example, as ALFONIC Ethoxylates (Conoco, Inc., Ponca City, OK) such as ALFONIC 1012-40 (where m is between about 8 and about 10 and where n is about 2.5); ALFONIC 1412-40 (where m is between about 10 and about 12 and where n is about 3); ALFONIC 610-50R (where m is between about 4 and about 8 and where n is about 3); ALFONIC 1214-GC-30 (where m is between about 10 and about 12 and where n is about 2); ALFONIC 1012-60 (where m is between about 8 and about 10 and where n is about 5.7); ALFONIC 1412-60 (where m is between about 10 and about 12 and where n is about 7) and ALFONIC 1218-70 (where m is between about 10 and about 16 and where n is about 10.7).

Numerous other nonionic polymeric ethoxylate surfactants are available, each having particular alkyl or alkylaryl pendant functions, and may also be used in the practice of the present invention since they are acknowledged to have oil emulsifying properties. Preferable properties of these usable surfactants include non-toxicity, miscibility with an anti-perspirant inorganic compound and ability to emulsify oils. Miscibility with dermatologically acceptable solvents such as alkyl alcohols with less than four carbon atoms is convenient for the preparation of liquid compositions although a waxlike stick of a substantially solid nonionic polymeric surfactant, possibly dispersed in a semi-solid inert carrier could be used. A preferred solvent is isopropanol, containing up to about 30 volume percent water.

Particularly preferred as nonionic polymeric surfactants in the practice of the present invention are the polymeric ethoxylates, too numerous to list completely herein, some of which are mentioned above, other examples being those of the IGEPAL series available from GAF Corp., N.Y., N.Y. such as nonylphenylpolyethoxyethanol having the formula:

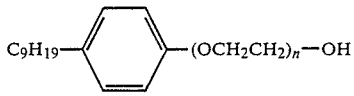

where n is about: 4 (IGEPAL CO-430); 9 (IGEPAL CO-630); 15 (IGEPAL CO-730); or 30 (IGEPAL CO-880). Another particular example of nonionic polymeric ethoxylate surfactant is also available from GAF Corp., N.Y., N.Y. and usable in the practice of the present invention is octylphenylpolyethoxyethanol (IGEPAL CA-630) having the formula:

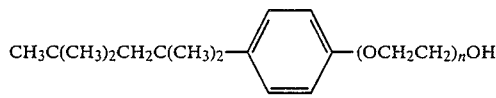

where n is about 10.

Nonionic polymeric ethoxylates which are usable in the practice of the present invention include those represented by the general formula:

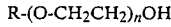

where n is between about 3 and about 30 and R is alkyl or alkylaryl having between about 6 and about 15 carbon atoms.

The nonionic polymeric ethoxylate surfactants bearing alkyl, alkylaryl or alkylaryloxy substituents and all having many similar oil emulsifying or "degreasing" characteristics, are preferred in the practice of the present invention.

The dermatologically acceptable volatile solvent preferably used in preparing the composition of the present invention comprises isopropanol although other alkyl alcohols having less than four carbon atoms are also usable as well as other solvents benign to the skin and compatible with these surfactants. The term "dermatologically acceptable" is used herein to indicate qualities of non-toxicity and absence of irritating effects upon the skin. The dermatologically acceptable volatile solvents may be used as mixtures containing, for example, less than about 50 volume percent water, a major desirability being the solubilization of antiperspirant and surfactant.

Numerous compositions were prepared comprising between about ten volume percent about ninety-nine volume percent nonionic polymeric ethoxylate surfactant; at least about 0.1 weight percent antiperspirant compound aluminum chloride hexahydrate; and up to about 89.9 volume percent aqueous isopropanol (containing about 30 volume percent water). The effectiveness of the compositions in enhancing leather covering tactile characteristics were found to depend somewhat on the concentration, but not the particular type, of nonionic polymeric ethoxylate. At nonionic polymeric ethoxylate surfactant concentrations significantly less than about 10 volume percent, the enhancement of leather covering tactile characteristics notably lessened. At nonionic polymeric ethoxylate concentrations higher than about 10 volume percent, optimal enhancement was not noticeably affected by variations in concentration. The nonionic polymeric ethoxylate surfactants ALFONIC 610-R and ALFONIC 1012-60, at 10 volume percent concentration were particularly found to be indistinguishably effective leather tactile enhancers when used for treatment of tennis racquet leather coverings.

A composition for enhancing the tactile characteristics of leather coverings is described as comprising: between about 10 volume percent and about 99.9 volume percent nonionic polymeric ethoxylate surfactant; at least about 0.1 weight percent antiperspirant inorganic compound and up to about 89.9 volume percent dermatologically acceptable volatile solvent.

The following examples, not meant to be limiting unless otherwise stated herein, are presented for a more complete understanding of the preferred embodiment of the present invention. In these examples the particular nonionic polymeric ethoxylate surfactant utilized had the formula:

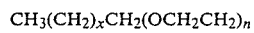

where x is between about 4 and about 8 and n is about 3 (ALFONIC 610-50R). The dermatologically acceptable volatile solvent utilized is referred to as isopropanol, but was, in fact, commercially available rubbing alcohol containing about 70 volume percent isopropanol and about 30 volume percent water.

EXAMPLE I

Two compositions were prepared. Composition A contained: about 10 volume percent nonionic polymeric ethoxylate (ALFONIC 610-50R); about 89.9 volume percent aqueous isopropanol (about 70 volume percent isopropanol); and about 0.5 weight percent aluminum chloride hexahydrate, an antiperspirant inorganic compound. Composition B contained about 10 volume percent nonionic polymeric ethoxylate (ALFONIC 610-50R) and about 90 volume percent aqueous isopropanol.

Six randomly chosen tennis players were each given a sample of Composition A and a sample of Composition B. The players were instructed to test each composition independently by first rubbing a quantity of a composition into the leather handle of their tennis racquet and then to dry the leather with a cloth or towel. Just prior to playing tennis, the players were instructed to rub their hands with the same composition used to treat their racquet and allow the solvent (isopropanol) to evaporate. Each player used each particular composition on different days and was later requested to make a verbal report on their perceived preferences developed over a week of testing for Composition A as compared to Composition B. Each of the six tennis players, after playing tennis on very hot Oklahoma July days, chose Composition A (with ethoxylate, antiperspirant and isopropanol), as being superior to Composition B (with ethoxylate and isopropanol). The importance of including antiperspirant in the composition was thus subjectively indicated. The tactile characteristics when tennis racquet handles and player hands were treated with Composition A were found to be excellent, superior to that of the untreated racquets, while permitting a sure racquet grip and allowing unimpeded changes of grip from forehand to backhand and vice-versa.

EXAMPLE II

A composition containing about 10 volume percent ethoxylate (ALFONIC 610-50R) and about 90 volume percent aqueous isopropanol (about 70 volume percent isopropanol) was dispersed into four bottles, two labelled as numeral 9 and two labelled as numeral 10. Two of the tennis players who had participated in the experiment of Example I were each given a sample labelled 9 and a sample labelled 10. The players were instructed as they were in Example I to evaluate sample 9 and sample 10 during tennis play. Both players later reported that samples 9 and 10 were adequate, but nevertheless inferior to the previously preferred sample they had tested before, i.e. inferior to Composition A from Example I. The preferability of antiperspirant inclusion in the composition of the present invention was again shown.

EXAMPLE III

Four tennis players were selected and given numerically coded compositions for leather treatment. Each player was given a designated Sample 11 (composed as was Composition A in Example I) and a designated Sample 12. Sample 12 contained about 99.5 volume percent aqueous isopropanol and about 0.5 weight percent aluminum chloride hexahydrate. The tennis players were instructed as were those in Example I and later reported that Sample 12 "didn't really work too well" and that they much preferred the results obtained with Sample 11.

This test was repeated with a new combination of six tennis players who each received a designated Sample 11 and designated Sample 12, prepared as described above. Again, every player later reported that the composition containing about 10 volume percent nonionic polymeric ethoxylate; about 89.5 volume percent aqueous isopropanol; and about 0.5 weight percent aluminum chloride hexahydrate was superior in enhancing the playable gripability of their tennis racquets. The preferability of including at least about 10 volume percent nonionic polymeric ethoxylate was thus subjectively shown.

The above Examples suggest that both the nonionic polymeric ethoxylate surfactant and the antiperspirant inorganic compound are desired to optimally enhance the tactile characteristics of tennis racquet leather handles during sports activity. By analogy with other sports played with implements having leather covered handles such as those of racquets or clubs, the composition and method of the present invention has a wide applicability. The leather covered handles of sports implements such as those used in tennis, golf, racquet ball, polo, hockey, or badminton, for example, should be tactually improved by use of the composition and method of the present invention.

Changes may be made in the procedures, the sequence of method steps or in the specific ingredients described herein without departing from the spirit and scope of the invention as described in the following claims.

What is claimed:

1. A method for enhancing the tactile characteristics of a leather covering comprising:
    applying a quantity of a composition to the leather covering, the composition comprising:
        between about 10 volume percent and about 99.9 volume percent nonionic polymeric ethoxylate surfactant;
        at least about 0.1 weight percent antiperspirant inorganic compound; and
        up to about 89.9 volume percent dermatologically acceptable volatile solvent; and
    rubbing the applied composition into the leather covering.

2. The method of claim 1 wherein the composition is defined further as comprising about 0.5 weight percent anti-perspirant inorganic compound.

3. The method of claim 1 wherein the nonionic polymeric ethoxylate surfactant is defined further as having the formula:

$$R\text{-}(O\text{-}CH_2CH_2)_n OH$$

where n is between about 3 and about 30 and R is alkyl or alkylaryl having between about 6 and about 15 carbon atoms.

4. The method of claim 3 wherein R is defined further as being alkyl and as having the formula:

$$CH_3(CH_2)_m CH_2$$

where m is between about 4 and about 16 and n is between about 3 and about 11.

5. The method of claim 4 wherein m is defined further as being between about 4 and about 8 and n is about 3.

6. The method of claim 1 wherein the composition is defined further as comprising between about 10 volume percent and about 15 volume percent nonionic polymeric ethoxylate surfactant and between about 84.5 volume percent and about 89.5 volume percent solvent.

7. The method of claim 1 wherein the leather covering is defined further as being that about the handle of a sports racquet or club intended to be held by at least one hand of an individual and wherein the method is defined further as:
    applying a quantity of the composition to at least one hand planned to be used in holding said racquet handle in performance of a sport; and
    allowing the solvent to evaporate from the applied composition.

8. The method of claim 1 wherein the antiperspirant inorganic compound is defined further as being aluminum chloride hexahydrate, aluminum chlorohydrate, or a mixture thereof.

9. The method of claim 1 wherein the solvent is defined further as comprising an alkyl alcohol having less than four carbon atoms.

10. The method of claim 1 wherein the solvent is defined further as comprising isopropanol and water.

11. The method of claim 7 wherein the sports racquet or club is defined further as being a tennis racquet, racquet ball racquet or golf club.

12. The method of claim 1 defined further to include the step of:
    drying the leather covering with a cloth.

* * * * *